United States Patent
Sumi et al.

(10) Patent No.: US 9,072,470 B2
(45) Date of Patent: Jul. 7, 2015

(54) ULTRASOUND DIAGNOSIS APPARATUS, ULTRASOUND IMAGE PROCESSING APPARATUS, IMAGE PROCESSING METHOD, IMAGE DISPLAY METHOD, AND COMPUTER PROGRAM PRODUCT

(75) Inventors: Atsushi Sumi, Otawara (JP); Fumiyasu Sakaguchi, Otawara (JP); Takuya Sasaki, Nasu-machi (JP); Kenichi Ichioka, Nasushiobara (JP); Akihiro Kakee, Nasushiobara (JP); Tomohisa Imamura, Nasushiobara (JP); Chihiro Shibata, Nasushiobara (JP); Kuramitsu Nishihara, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 373 days.

(21) Appl. No.: 12/688,220

(22) Filed: Jan. 15, 2010

(65) Prior Publication Data

US 2010/0185091 A1    Jul. 22, 2010

(30) Foreign Application Priority Data

Jan. 20, 2009    (JP) ................. 2009-010245

(51) Int. Cl.
*A61B 8/00* (2006.01)
*G06K 9/00* (2006.01)
(Continued)

(52) U.S. Cl.
CPC ... *A61B 8/14* (2013.01); *A61B 8/08* (2013.01); *A61B 8/0883* (2013.01); *A61B 8/463* (2013.01);
(Continued)

(58) Field of Classification Search
CPC .......... A61B 8/08; A61B 8/0883; A61B 8/14; A61B 8/463; A61B 8/469; A61B 8/483; G01S 15/8993; G01S 7/52063; G01S 7/52074; G01S 7/52087; G06T 11/60; G06T 15/06; G06T 15/08; G06T 3/4038
USPC .................... 600/437, 441, 443; 382/128
See application file for complete search history.

(56) References Cited

U.S. PATENT DOCUMENTS 6,544,178 B1 *    4/2003    Grenon et al. ................. 600/443
2008/0177182 A1 *    7/2008    Takimoto et al. ............. 600/441
(Continued)

FOREIGN PATENT DOCUMENTS

EP    1 582 150 A1    10/2005
JP    2000-132664    5/2000
(Continued)

OTHER PUBLICATIONS

English translation of JP 2007-034518.*
(Continued)

*Primary Examiner* — Katherine Fernandez
(74) *Attorney, Agent, or Firm* — Oblon, McClelland, Maier & Neustadt, L.L.P.

(57) ABSTRACT

As an ROI for display and an ROI for valve observation as well as a projecting direction are input, a volume-rendering processing unit creates a first image in the ROI for display through volume rendering processing, and the ray-tracing processing unit creates a second image in the ROI for valve observation through ray tracing processing. An image compositing unit then creates a composite image by compositing the first image and the second image, and the composite image created by the image compositing unit (13) is displayed on a monitor.

12 Claims, 8 Drawing Sheets

(51) Int. Cl.
  *A61B 8/14* (2006.01)
  *A61B 8/08* (2006.01)
  *G01S 15/89* (2006.01)
  *G06T 15/06* (2011.01)
  *G06T 15/08* (2011.01)
  *G01S 7/52* (2006.01)

(52) U.S. Cl.
  CPC ............... *A61B 8/469* (2013.01); *A61B 8/483* (2013.01); *G01S 7/52063* (2013.01); *G01S 7/52074* (2013.01); *G01S 7/52087* (2013.01); *G01S 15/8993* (2013.01); *G06T 15/06* (2013.01); *G06T 15/08* (2013.01)

(56) References Cited

U.S. PATENT DOCUMENTS

2008/0317316 A1* 12/2008 Ohuchi et al. ............... 382/131
2010/0099991 A1* 4/2010 Snyder ........................ 600/454
2011/0301451 A1* 12/2011 Rohling ....................... 600/424

FOREIGN PATENT DOCUMENTS

| | | |
|---|---|---|
| JP | 2004-195082 | 7/2004 |
| JP | 2007-34518 | 2/2007 |
| JP | 2007-82649 | 4/2007 |
| JP | 2007-289569 | 11/2007 |
| JP | 2008-259605 | 10/2008 |
| JP | 2008-272483 | 11/2008 |
| WO | WO 2008/044173 A1 | 4/2008 |
| WO | WO 2008/081558 A1 | 7/2008 |

OTHER PUBLICATIONS

Japanese Office Action issued Oct. 15, 2013, in Japan Patent Application No. 2009-267651 (with English translation).
Communication pursuant to Article 94(3) EPC issued Oct. 7, 2013, in Application No. 10 000 478.7-1660.

* cited by examiner

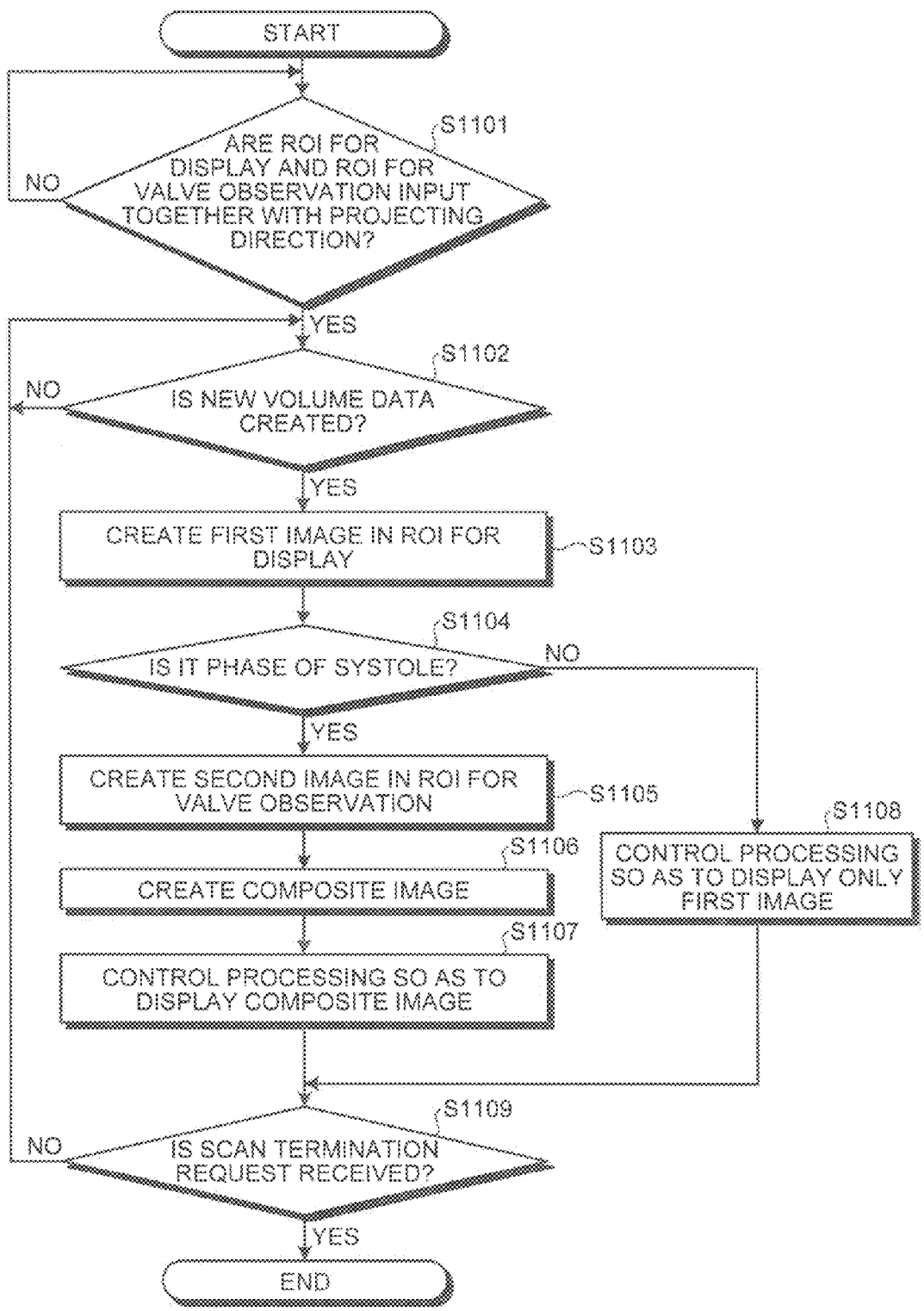

ULTRASOUND DIAGNOSIS APPARATUS, ULTRASOUND IMAGE PROCESSING APPARATUS, IMAGE PROCESSING METHOD, IMAGE DISPLAY METHOD, AND COMPUTER PROGRAM PRODUCT

CROSS-REFERENCE TO RELATED APPLICATIONS

This application is based upon and claims the benefit of priority from the prior Japanese Patent Application No. 2009-10245, filed on Jan. 20, 2009; the entire contents of which are incorporated herein by reference.

BACKGROUND OF THE INVENTION

1. Field of the Invention

The present invention relates to an ultrasound diagnosis apparatus, an ultrasound image processing apparatus, an image processing method, an image display method, and a computer program product.

2. Description of the Related Art

Conventionally, it has been a practice to create a two-dimensional image in which three-dimensional information is reflected, through rendering processing from volume data. For example, according to an ultrasound diagnosis apparatus that creates a three-dimensional ultrasound image by performing a scan with ultrasound waves three-dimensionally (for example, see JP-A 2000-132664 (KOKAI), when a doctor performs diagnostic imaging, a two-dimensional ultrasound image is created from a three-dimensional ultrasound image through rendering processing, and the created two-dimensional ultrasound image is displayed on a monitor.

As a typical method of such rendering processing, a ray tracing method and a volume rendering method can be listed.

According to the ray tracing method, a part corresponding to a surface of a structure is specified on each voxel in volume data, and then an angle of the part specified as the surface of the structure is calculated. A two-dimensional image of a projective plane in which three-dimensional information is reflected is then created by summing brightness values of reflected light that is light emitted from a virtual light source set at a view point reaching the projective plane while reflecting from the surface of the structure specified on each voxel. According to the ray tracing method, an artificial simulation of reflection of light produced on a surface of a structure is executed, so that shades of the structure can be naturally expressed.

According to the volume rendering method, a two-dimensional image of a projective plane in which three-dimensional information is reflected is created by performing multiplication computing of opacity and shading values from a view point continuously in a projecting direction after calculating opacity and a shading value based on each voxel value by considering a state of attenuation and shading of light from the view point when passing through each voxel. According to the volume rendering method, a three-dimensional structure of an object is visually expressed with brightness or variations of color.

Comparing the volume rendering method and the ray tracing method by which it takes some time as a processing time to trace light from a light source, a process procedure can be simplified according to the volume rendering method. For this reason, generally, an ultrasound diagnosis apparatus that creates a three-dimensional ultrasound image uses the volume rendering method as rendering processing to ensure a real-time response when displaying a two-dimensional ultrasound image.

For example, when observing a heart valve with an ultrasound diagnosis apparatus, according to the volume rendering method, contours of the heart valve are displayed in dark color, so that the structure of the heart valve can be visually recognized. Moreover, when performing the volume rendering method, unwanted signals can be removed by limiting a region of interest and executing threshold processing, so that the structure of the heart valve can be more visually recognized.

Specifically, when intending to observe a heart valve, and if a structure (for example, myocardium) that is to be an obstruction is present between the heart valve and a view point; as the obstruction is removed by adjusting a region of interest on which a volume rendering method is to be performed, a doctor can observe the heart valve without the doctor's view being obstructed by the obstruction. Furthermore, according to the volume rendering method, when visibility of a heart valve is decreased due to a low signal that is to be a noise, the visibility of the heart valve for a doctor can be improved by removing the noise through threshold processing.

In this way, a doctor can observe a heart valve without the doctor's view being obstructed by an obstruction or a noise, by optimizing a region of interest and threshold processing when performing the volume rendering. For example, a structure behind a heart valve obstructed by the closed heart valve turns visible in a state that the heart valve is open. However, because a heart valve and a structure behind the heart valve are expressed in similar colors on a two-dimensional ultrasound image created by the volume rendering method; when diagnosing whether regurgitation occurs in the heart of a subject, a region of interest needs to be further adjusted. Specifically, as edges of a region of interest are adjusted to come to heart chambers present in front of and behind the heart valve, there is no structure obstructing a view in front of and behind of the heart valve, so that a background color can be seen in a state that the heart valve is open, and an open-close state of the heart valve can be recognized by determining whether the background color is visible.

In this way, by adjusting a region of interest on which the volume rendering method is to be performed, a doctor can confirm an open-close state of a heart valve by using a two-dimensional ultrasound image created from a three-dimensional ultrasound image by the volume rendering method.

The conventional technologies described above have a problem that it is sometimes difficult to confirm an open-close state of a heart valve in some cases. In other words, even if edges of a region of interest are adjusted to come to heart chambers present in front of and behind the heart valve; when regurgitation is small, contours of the heart valve are displayed in a dark color similarly to a background color. For this reason, according to the volume rendering method used for ensuring a real-time response, it becomes difficult to distinguish between a color originating from a heart chamber and a color originating from contours of the heart valve, among background colors visually recognized between the structures of the heart valve.

Therefore, the present invention has been made for solving the problem of the conventional technologies described above, and an object of the present invention is to provide an ultrasound diagnosis apparatus, an ultrasound image processing apparatus, an image processing method, an image display method, and a computer program product, by which visibility of an open-close state of a heart valve on an ultrasound image can be improved.

SUMMARY OF THE INVENTION

According to an aspect of the present invention, an ultrasound diagnosis apparatus includes an image processing unit by which when a first region of interest that is a region of interest when displaying onto a certain display unit an ultrasound image created based on a reflected wave of an ultrasound wave transmitted to a subject from an ultrasound probe, and a second region of interest that is a region of interest overlapping with the first region of interest and for observing a certain subject portion included in the ultrasound image, as well as a projecting direction, are received from a certain input unit, a first image is created by performing volume rendering processing on an ultrasound image in the first region of interest onto a projective plane along the projecting direction, and a second image on which motion of the certain subject portion can be identified is created from an ultrasound image in the second region of interest; and a system control unit that controls processing so as to display the first image and the second image created by the image processing unit in a superimposed manner onto the certain display unit.

According to another aspect of the present invention, an ultrasound image processing apparatus includes an image processing unit by which when a first region of interest that is a region of interest when displaying onto a certain display unit an ultrasound image created based on a reflected wave of an ultrasound wave transmitted to a subject from an ultrasound probe, and a second region of interest that is a region of interest overlapping with the first region of interest and for observing a certain subject portion included in the ultrasound image, as well as a projecting direction, are received from a certain input unit, a first image is created by performing volume rendering processing on an ultrasound image in the first region of interest onto a projective plane along the projecting direction, and a second image on which motion of the certain subject portion can be identified is created from an ultrasound image in the second region of interest; and a system control unit that controls processing so as to display the first image and the second image created by the image processing unit in a superimposed manner onto the certain display unit.

According to still another aspect of the present invention, an ultrasound image processing apparatus includes an image processing unit by which a first image is created by performing volume rendering processing on an image in a first region of interest based on an ultrasound image onto a projective plane along a projecting direction, and a second image on which motion of a certain subject portion included in the ultrasound image can be identified is created from an image in a second region of interest that is a region of interest for observing the certain subject portion.

According to still another aspect of the present invention, an image processing method includes an image creating step of creating a first image by performing volume rendering processing onto a projective plane along a projecting direction on an ultrasound image in a first region of interest that is a region of interest when displaying onto a certain display unit an ultrasound image of a subject created based on a reflected wave of an ultrasound wave transmitted from an ultrasound probe, and creating a second image, on which motion of a certain subject portion included in the ultrasound image can be identified, from an ultrasound image in a second region of interest that is a region of interest overlapping with the first region of interest and for observing the certain subject portion, when receiving the first region of interest and the second region of interest as well as the projecting direction from a certain input unit; and a display controlling step of controlling processing so as to display the first image and the second image created by the image creating step in a superimposed manner onto the certain display unit.

According to still another aspect of the present invention, an image display method includes superimposing and displaying a first image created by performing volume rendering processing on an image in a first region of interest based on an ultrasound image onto a projective plane along a projecting direction, and a second image on which motion of a certain subject portion included in the ultrasound image can be identified, the second image being created from an image in a second region of interest that is a region of interest for observing the certain subject portion.

According to still another aspect of the present invention, an image display method includes a display controlling step of controlling processing so as to display a first image and a second image in a superimposed manner on a certain display unit when receiving a first region of interest and a second region of interest as well as a projecting direction from a certain input unit, the first region of interest being a region of interest when displaying onto the certain display unit an ultrasound image of a subject created based on a reflected wave of an ultrasound wave transmitted from the ultrasound probe, the second region of interest being a region of interest overlapping with the first region of interest and for observing a certain subject portion included in the ultrasound image, the first image being created by performing volume rendering on an ultrasound image in the first region of interest onto a projective plane along the projecting direction, and the second image, on which motion of the certain subject portion can be identified, being created from an ultrasound image in the second region of interest.

According to still another aspect of the present invention, a computer program product having a computer readable medium including a plurality of instructions for executing image processing executable by a computer, wherein the instructions, when executed by a computer, cause the computer to perform: creating a first image by performing volume rendering processing onto a projective plane along a projecting direction on an ultrasound image in a first region of interest that is a region of interest when displaying onto a certain display unit an ultrasound image of a subject created based on a reflected wave of an ultrasound wave transmitted from an ultrasound probe to a subject, and creating a second image, on which motion of a certain subject portion included in the ultrasound image can be identified, from an ultrasound image in a second region of interest that is a region of interest overlapping with the first region of interest and for observing the certain subject portion, when receiving the first region of interest and the second region of interest as well as the projecting direction from a certain input unit; and controlling processing so as to display the first image and the second image in a superimposed manner onto the certain display unit.

BRIEF DESCRIPTION OF THE DRAWINGS

FIG. 11 is a flowchart for explaining processing performed by the ultrasound diagnosis apparatus according to the third embodiment.

DETAILED DESCRIPTION OF THE INVENTION

Exemplary embodiments of an ultrasound diagnosis apparatus, an ultrasound image processing apparatus, an image processing method, an image display method, and a computer program product according to the present invention will be explained below in detail with reference to the accompanying drawings.

Figure 1:
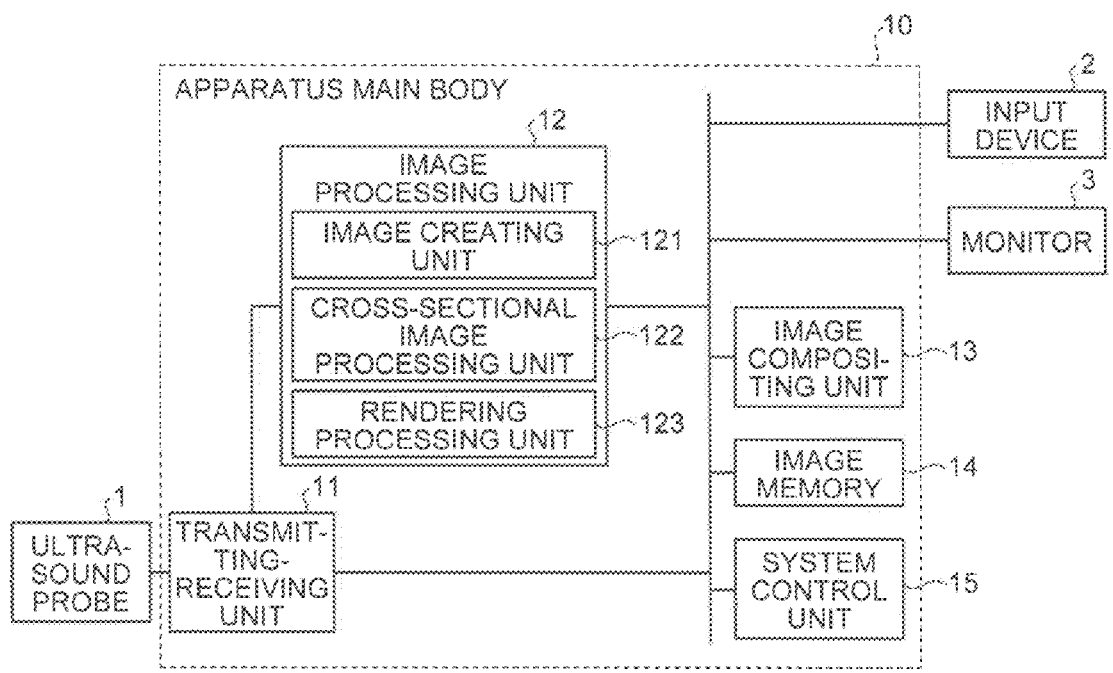
FIG. 1 is a schematic diagram for explaining a configuration of an ultrasound diagnosis apparatus according to a first embodiment of the present invention.

First of all, a configuration of an ultrasound diagnosis apparatus according to a first embodiment of the present invention is explained below. FIG. 1 is a schematic diagram for explaining a configuration of the ultrasound diagnosis apparatus according to the first embodiment. As shown in FIG. 1, the ultrasound diagnosis apparatus according to the first embodiment includes an ultrasound probe 1, an input device 2, a monitor 3, and an apparatus main body 10.

The ultrasound probe 1 includes a plurality of built-in ultrasound vibration elements that a plurality of vibration element cells is integrated. Each ultrasound vibration element generates an ultrasound wave, and transmits the generated ultrasound wave to the inside of a subject as an ultrasound beam, and receives a signal of a reflected wave from internal tissue of the subject.

The first embodiment is explained below in a case of using a two-dimensional ultrasound probe that includes ultrasound vibration elements arranged in a matrix as the ultrasound probe 1, thereby three-dimensionally scanning the inside of a subject. However, the present invention can be applied to a case of using a one-dimensional ultrasound probe that includes ultrasound vibration elements arranged in a row as the ultrasound probe 1, and rocking the ultrasound vibration elements arranged in a row, thereby three-dimensionally scanning the inside of a subject.

The monitor 3 is a display device that includes a monitor for displaying an ultrasound image created by the apparatus main body 10, and displaying a Graphical User Interface (GUI) for receiving a command from a doctor or an engineer who is an operator of the ultrasound diagnosis apparatus.

The input device 2 includes a panel switch, a touch command screen, a foot switch, a trackball, and the like, receives various setting requests from an operator of the ultrasound diagnosis apparatus, and inputs each of the received setting requests into the apparatus main body 10.

The apparatus main body 10 is a device that creates an ultrasound image based on a reflected wave received by the ultrasound probe 1; and includes a transmitting-receiving unit 11, an image processing unit 12, an image compositing unit 13, an image memory 14, and a system control unit 15, as shown in FIG. 1.

The transmitting-receiving unit 11 is connected to the ultrasound probe 1, and generates a high voltage pulse every predetermined delay time under the control of the system control unit 15, which will be described later. The high voltage pulse generated by the transmitting-receiving unit 11 is sequentially applied to the ultrasound vibration elements built in the ultrasound probe 1, thereby generating an ultrasound wave by each ultrasound vibration element.

Moreover, the transmitting-receiving unit 11 performs gain correction processing, analog-to-digital (A/D) conversion processing, and phase addition processing on a signal of a reflected wave received by the ultrasound probe 1, and creates reflected wave data. Specifically, the transmitting-receiving unit 11 creates three-dimensional reflected wave data obtained by three-dimensionally scanning a subject.

The image processing unit 12 is a processing unit that creates various image data by executing various image processing from three-dimensional reflected wave data created by the transmitting-receiving unit 11 under the control of the system control unit 15, which will be described later; and includes an image creating unit 121, a cross-sectional image processing unit 122, and a rendering processing unit 123.

The image creating unit 121 creates a three-dimensional ultrasound image from three-dimensional reflected wave data created by the transmitting-receiving unit 11.

The cross-sectional image processing unit 122 creates a Multi Planar Reconstruction (MPR) image corresponding to a predetermined cross-sectional direction from a three-dimensional ultrasound image created by the image creating unit 121.

The rendering processing unit 123 creates a two-dimensional image on a certain projective plane in which three-dimensional information is reflected (hereinafter, "rendering image") through rendering processing from a three-dimensional ultrasound image created by the image creating unit 121. The rendering processing unit 123 will be described later in detail.

Under the control of the system control unit 15, the image compositing unit 13 creates composite image data that various image data created by the image processing unit 12 are composited.

The image memory 14 stores therein image data created by the image processing unit 12, and composite image data created by the image compositing unit 13.

The system control unit 15 controls processing performed by the transmitting-receiving unit 11, the image processing unit 12, and the image compositing unit 13, based on various setting requests input from the input device 2.

For example, a request to set a high voltage to be generated by the transmitting-receiving unit 11, a request to set a cross-sectional direction when the cross-sectional image processing unit 122 creates an MPR image, a request to set a projecting direction for determining a projective plane when the rendering processing unit 123 creates a rendering image, and a request to set image data to be composited when the image compositing unit 13 creates composite image data are listed among various setting requests input from an operator via the input device 2. Moreover, the system control unit 15 causes the monitor 3 to display image data and composite image data stored by the image memory 14 based on a display request input from the operator via the input device 2.

Figure 2:
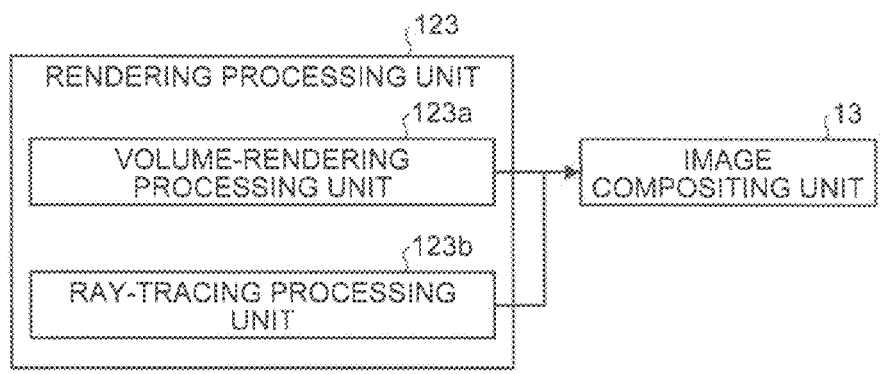
FIG. 2 is a schematic diagram for explaining a configuration of a rendering processing unit according to the first embodiment.
Figure 3A:
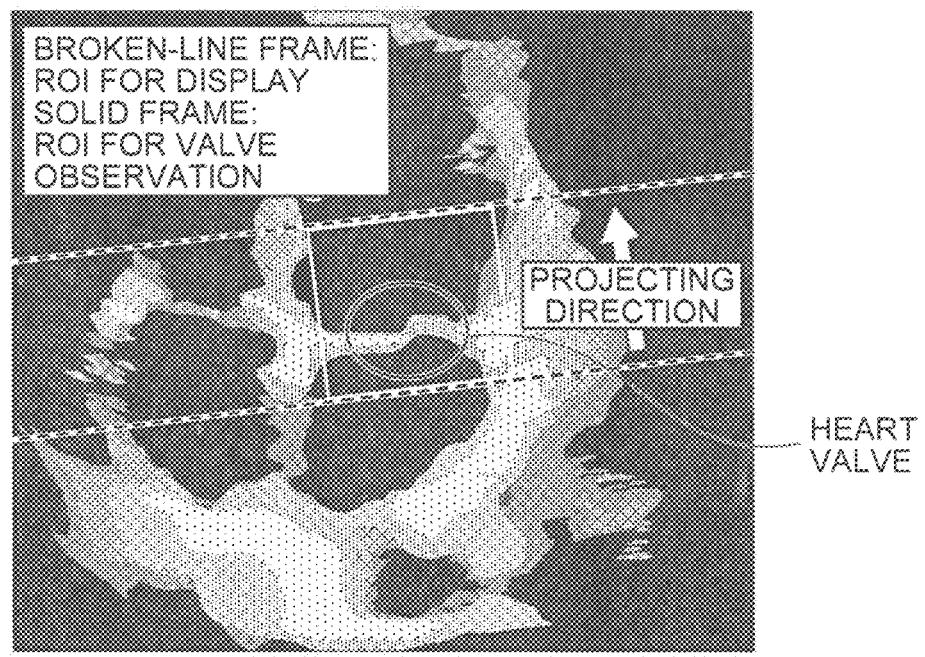
FIGS. 3A and 3B are schematic diagrams for explaining a Region Of Interest (ROI) for display and an ROI for valve observation according to the first embodiment.
Figure 3B:
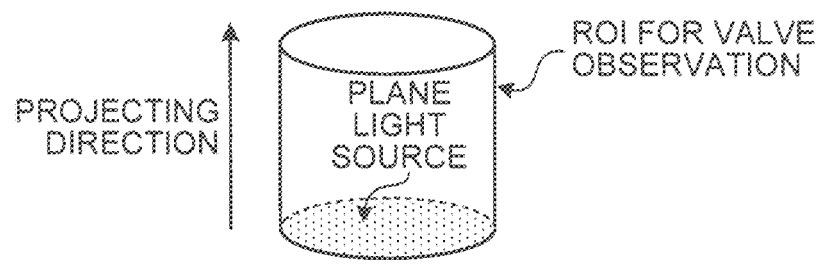
Figure 4A:
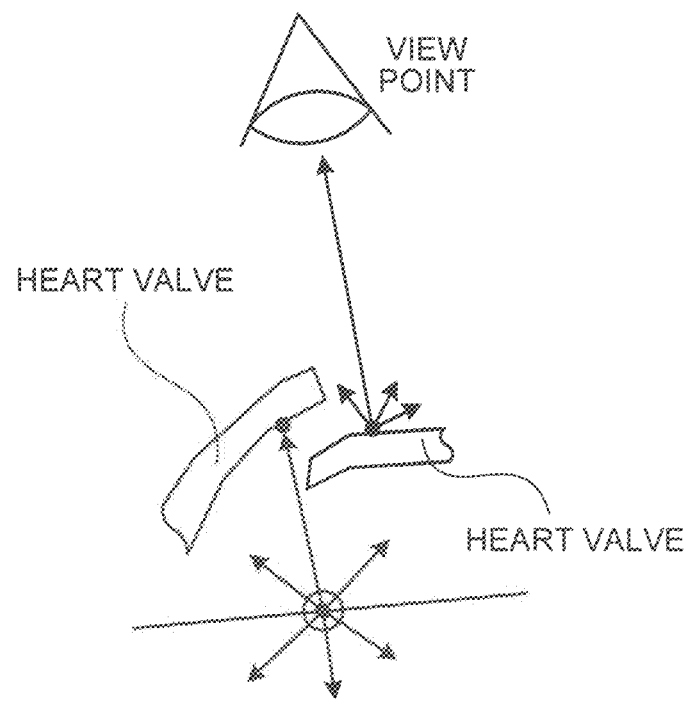
FIGS. 4A and 4B are schematic diagrams for explaining a second image and a composite image according to the first embodiment.
Figure 4B:
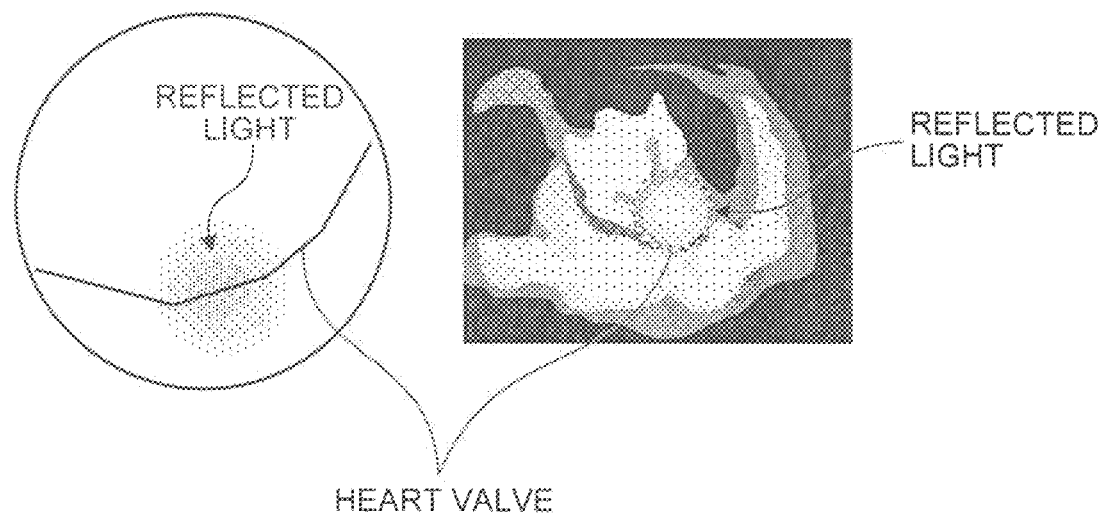

The ultrasound diagnosis apparatus according to the first embodiment has a main feature that when displaying on the monitor 3 image data created from three-dimensional reflected wave data obtained by three-dimensionally scanning the heart of a subject, visibility of an open-close state of a heart valve on an ultrasound image can be improved by executing processing by the rendering processing unit 123, which is explained below. The main feature is explained below with reference to FIGS. 2 to 4. FIG. 2 is a schematic diagram for explaining a configuration of the rendering processing unit according to the first embodiment; FIGS. 3A and 3B are schematic diagrams for explaining an ROI for display and an ROI for valve observation according to the first embodiment; and FIGS. 4A and 4B are schematic diagrams for explaining a second image and a composite image according to the first embodiment.

As shown in FIG. 2, the rendering processing unit 123 according to the first embodiment includes a volume-rendering processing unit 123a, and a ray-tracing processing unit 123b.

The volume-rendering processing unit 123a creates a rendering image through volume rendering processing from a three-dimensional ultrasound image created by the image creating unit 121; and the ray-tracing processing unit 123b creates a rendering image through ray tracing processing from a three-dimensional ultrasound image created by the image creating unit 121.

When an operator inputs a request to set a cross-sectional direction and a request to display an MPR image via the input device 2, under the control of the system control unit 15, the cross-sectional image processing unit 122 creates an MPR image in the set cross-sectional direction, and then the monitor 3 displays thereon the MPR image created by the cross-sectional image processing unit 122.

The operator then refers to the MPR image displayed on the monitor 3, and inputs via the input device 2 a Region Of Interest (ROI) for display (see a broken-line frame in FIG. 3A) that is a region of interest when displaying on the monitor 3 a rendering image of a three-dimensional ultrasound image on which the heart of a subject is rendered, and an ROI for valve observation (see a solid-line frame in FIG. 3A) that is an ROI for observing a heart valve in the heart of the subject and overlapping with the ROI for display, as well as a projecting direction for defining a projective plane.

The system control unit 15 converts "a two-dimensional ROI for display and a two-dimensional ROI for valve observation" set by the operator who refers to the MPR image into "a three-dimensional ROI for display and a three-dimensional ROI for valve observation" on a three-dimensional ultrasound image. For example, as shown in FIG. 3A, the system control unit 15 converts a region of a three-dimensional ultrasound image positioned between parallel two cross sections orthogonal to the projecting direction through broken lines that are input when setting a two-dimensional ROI for display, into a three-dimensional ROI for display.

Moreover, as shown in FIG. 3B, the system control unit 15 converts a region of the three-dimensional ultrasound image in a circular column that a rectangle input when setting a two-dimensional ROI for valve observation is rotated with respect to a rotational axis in the projecting direction into a three-dimensional ROI for valve observation. In the three-dimensional ROI for valve observation, as shown in FIG. 3B, a virtual plane light source positioned opposite to the projecting direction is set. An explanation of the virtual plane light source will be described later.

The ROI for valve observation is set such that the heart valve is to be positioned between the virtual plane light source and the projective plane. Moreover, to reduce a load of the ray tracing processing, it is desirable that the ROI for valve observation is set as a narrower region than the ROI for display.

A region of the three-dimensional ROI converted from the two-dimensional ROI input and set on an MPR image can be arbitrarily set by the operator, for example, a spherical surface, a plane surface, or a region surrounded with a spherical surface and a plane surface.

Returning to FIG. 2, the volume-rendering processing unit 123a creates a first image by performing the volume rendering processing on a three-dimensional ultrasound image in a three-dimensional ROI for display onto a projective plane in the projecting direction, under the control of the system control unit 15. Specifically, to render attenuation and a shading state of light set in the projecting direction from a view point toward a projective plane when passing through each voxel of a three-dimensional ultrasound image, the volume-rendering processing unit 123a calculates opacity and a shading value based on each voxel value. The volume-rendering processing unit 123a then creates a volume rendering image in a three-dimensional ROI for display as a first image by performing multiplication computing of the calculated opacity and the calculated shading value continuously along the projecting direction from the view point toward the projective plane.

The ray-tracing processing unit 123b creates a second image on which motion (open-close state) of the heart valve can be identified, from a three-dimensional ultrasound image in a three-dimensional ROI for valve observation, under the control of the system control unit 15. In other words, under the control of the system control unit 15, the ray-tracing processing unit 123b creates a second image by performing the ray tracing processing on the three-dimensional ultrasound image in the three-dimensional ROI for valve observation onto a projective plane with a virtual light source. Specifically, the ray-tracing processing unit 123b specifies a part corresponding to a surface of a structure (such as myocardium or valve) on each voxel of a three-dimensional ultrasound image, and calculates an angle of the part specified as the surface of the structure. The ray-tracing processing unit 123b then creates a ray tracing image in the three-dimensional ROI for valve observation as a second image by summing brightness values of reflected light that is light emitted from a virtual light source set at a view point reaching the projective plane while reflecting from the surface of the structure specified on each voxel.

In other words, according to the ray tracing processing, as shown in FIG. 4A, because light from the plane light source is reflected by the surface of the heart valve, for example, if the heart valve is slightly open due to regurgitation, a state that the heart valve is open is detected as a leak of light at the view point.

The image compositing unit 13 creates a composite image that a first image created by the volume-rendering processing unit 123a and a second image created by the ray-tracing processing unit 123b are composited. Accordingly, for example, as shown in FIG. 4B, a state that the heart valve is slightly open due to valvular incompetence is rendered on the composite image with a reflected light leaked from a gap of the heart valve originating in the second image, even when an open-close state of the heart valve is not clear only on the first image.

The system control unit 15 controls processing so as to store a composite image created by the image compositing unit 13 into the image memory 14, and to display the composite image onto the monitor 3.

Figure 5:
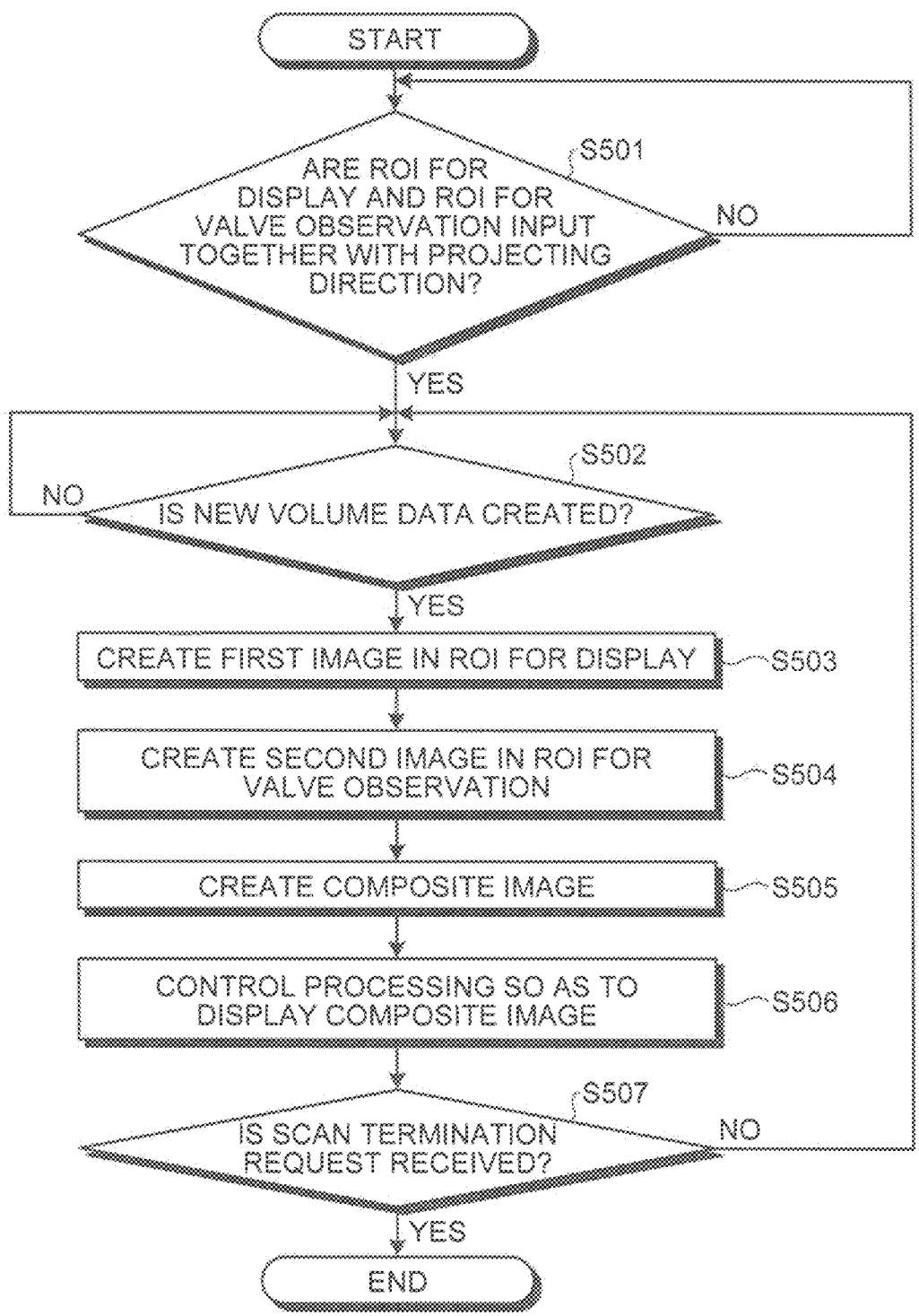
FIG. 5 is a flowchart for explaining processing performed by the ultrasound diagnosis apparatus according to the first embodiment.

Processing performed by the ultrasound diagnosis apparatus according to the first embodiment is explained below with reference to FIG. 5. FIG. 5 is a flowchart for explaining processing performed by the ultrasound diagnosis apparatus according to the first embodiment. A case explained in FIG. 5 is that the above processing of creating "a first image, a second image, and a composite image" is executed in real time on a three-dimensional ultrasound image (volume data) created along a time sequence through a three-dimensional scan of a subject with an ultrasound wave.

As shown in FIG. 5, according to the ultrasound diagnosis apparatus according to the first embodiment, when a scan is started, and then an ROI for display and an ROI for valve observation as well as a projecting direction are set on an MPR image of a three-dimensional ultrasound image by an operator via the input device 2 (Yes at Step S501), the system control unit 15 converts "a two-dimensional ROI for display and a two-dimensional ROI for valve observation" into "a three-dimensional ROI for display and a three-dimensional ROI for valve observation", and then determines whether new volume data is created (Step S502).

If new volume data is not created (No at Step S502), the system control unit 15 waits until new volume data is created. By contrast, if new volume data is created (Yes at Step S502), the system control unit 15 causes the rendering processing unit 123 and the image compositing unit 13 to start processing.

Precisely, under the control of the system control unit 15, the volume-rendering processing unit 123a creates a first image in the (three-dimensional) ROI for display through the volume rendering processing (Step S503).

The ray-tracing processing unit 123b then creates a second image in the (three-dimensional) ROI for valve observation through the ray tracing processing, under the control of the system control unit 15 (Step S504).

After that, the image compositing unit 13 creates a composite image by compositing the first image and the second image (Step S505), and then the system control unit 15 controls processing so as to display the composite image created by the image compositing unit 13 onto the monitor 3 (Step S506).

The system control unit 15 then determines whether a scan termination request is received from the operator via the input device 2 (Step S507); if scan termination request is not received (No at Step S507), the system control unit 15 goes back to Step S502, and waits until new volume data is created.

By contrast, if the scan termination request is received (Yes at Step S507), the system control unit 15 terminates the processing.

As described above, according to the first embodiment, when an ROI for display and an ROI for valve observation as well as a projecting direction are input; under the control of the system control unit 15, the volume-rendering processing unit 123a creates a first image in the ROI for display through the volume rendering processing; and the ray-tracing processing unit 123b creates a second image in the ROI for valve observation through the ray tracing processing, under the control of the system control unit 15. The image compositing unit 13 then creates a composite image by compositing the first image and the second image, and the system control unit 15 controls processing so as to display the composite image created by the image compositing unit 13 onto the monitor 3.

Accordingly, on the composite image, the structure of the heart valve is rendered according to the first image, and a state that the heart valve is not closed is clearly rendered as a state that reflected light is leaked and seen according to the second image, which is a ray tracing image that a plane light source is set behind the heart valve viewed in the view point direction, so that visibility of an open-close state of the heart valve on an ultrasound image can be improved as described in the above main feature. Moreover, because the ray tracing processing is performed by limiting to an ROI for valve observation, decrease in the realtime response due to the ray tracing processing can be suppressed, and a composite image for diagnostic imaging can be speedily created and displayed.

As a subject portion of which a composite image is to be created and displayed by using the volume rendering processing and the ray tracing processing according to the first embodiment, it can be applied to various subject portions as well as a heart valve. Moreover, the first embodiment can be applied to a case where an ROI for display is identical to an ROI for valve observation. Furthermore, the first embodiment can be applied even when a light source of the ray tracing processing is a light source other than a plane light source (for example, a point light source, a line light source, or a polyhedron light source).

Figure 6:
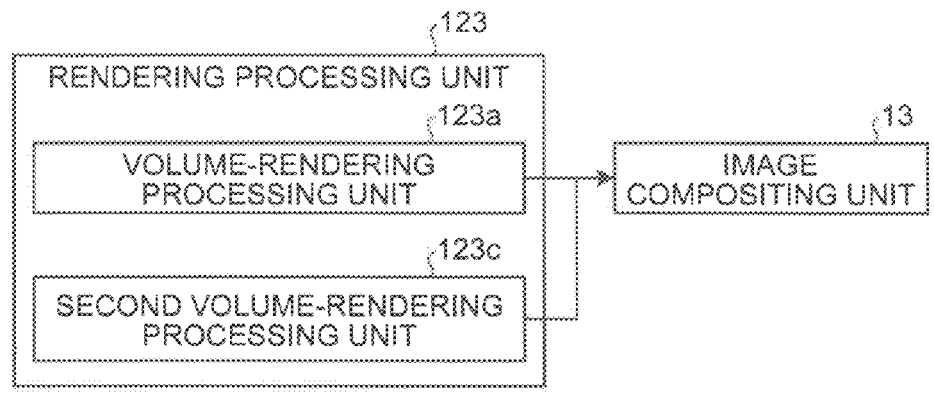
FIG. 6 is a schematic diagram for explaining a configuration of a rendering processing unit according to a second embodiment of the present invention.
Figure 7A:
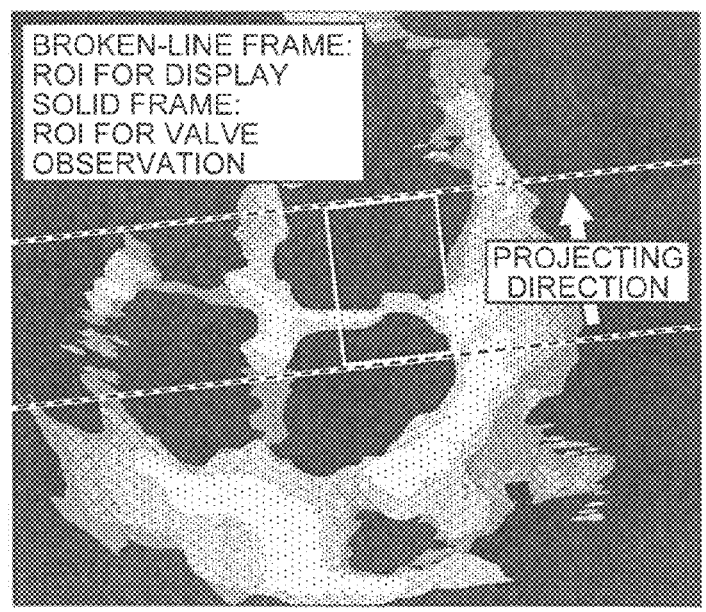
FIGS. 7A and 7B are schematic diagrams for explaining an ROI for display and an ROI for valve observation according to the second embodiment.
Figure 7B:
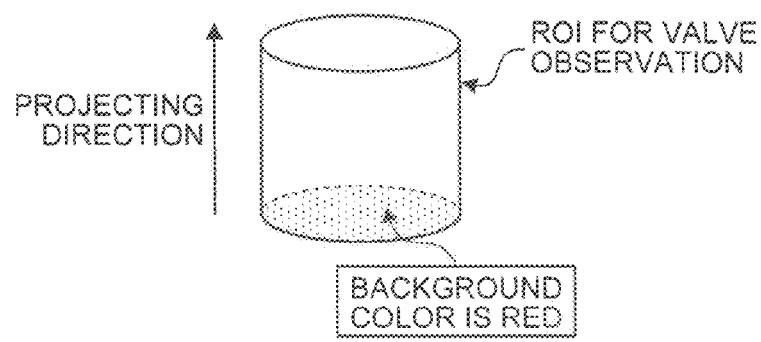
Figure 8:
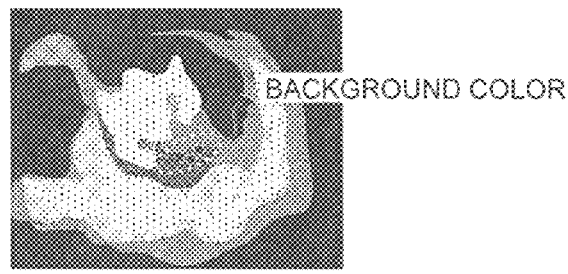
FIG. 8 is a schematic diagram for explaining a composite image according to the second embodiment.

A second embodiment of the present invention is explained below in a case where a second image on which motion (open-close state) of a heart valve can be identified is created from a three-dimensional ultrasound image in a three-dimensional ROI for valve observation by a method different from the first embodiment with reference to FIGS. 6 to 8. FIG. 6 is a schematic diagram for explaining a configuration of a rendering processing unit according to the second embodiment; FIGS. 7A and 7B are schematic diagrams for explaining an ROI for display and an ROI for valve observation according to the second embodiment; and FIG. 8 is a schematic diagram for explaining a composite image according to the second embodiment.

As shown in FIG. 6, differing from the first embodiment, the rendering processing unit 123 according to the second embodiment includes a second volume-rendering processing unit 123c, instead of the ray-tracing processing unit 123b. Precisely, according to the second embodiment, a second image on which motion (open-close state) of a heart valve can be identified is created from a three-dimensional ultrasound image in a three-dimensional ROI for valve observation through processing performed by the second volume-rendering processing unit 123c.

To begin with, as shown in FIG. 7A, according to the second embodiment, similarly to the first embodiment, an MPR image created from a three-dimensional ultrasound image is displayed on the monitor 3, and then "a two-dimensional ROI for display and a two-dimensional ROI for valve observation" as well as a projecting direction are set by an operator who refers to the MPR image. The system control unit 15 then converts "the two-dimensional ROI for display and the two-dimensional ROI for valve observation" into "a three-dimensional ROI for display and a three-dimensional ROI for valve observation.

The ROI for valve observation is set such that the heart valve is to be positioned between the projective plane and a plane opposite to the projective plane. Moreover, when viewing from a view point of the projective plane a region with which the heart valve overlaps when it is closed, it is desirable that the ROI for valve observation is to be set not to include obstruction (for example, myocardium) as much as possible.

Furthermore, the second embodiment can be applied to a case where an ROI for display is identical to an ROI for valve observation.

The volume-rendering processing unit 123a creates a first image by performing the volume rendering processing on a three-dimensional ultrasound image in a three-dimensional ROI for display, similarly to the first embodiment.

The second volume-rendering processing unit 123c creates a second image by performing the volume rendering processing on a three-dimensional ultrasound image in a three-dimensional ROI for valve observation. As shown in FIG. 7B, the second volume-rendering processing unit 123c creates a second image by making a color tone for rendering a plane opposite to the projective plane into a different color tone (for example, red) that is different from a color tone (for example, grayscale) when rendering the first image. Accordingly, a part that the heart valve is not closed can be rendered as a red background color on the second image. The background color can be arbitrarily set by the operator.

The image compositing unit 13 creates a composite image by compositing a first image created by the volume-rendering processing unit 123a and a second image created by the second volume-rendering processing unit 123c. Accordingly, for example, as shown in FIG. 8, a state that the heart valve is slightly open caused by regurgitation is clearly rendered on the composite image with a red background color originating in the second image, even when an open-close state of the heart valve is not clear only on the first image.

The system control unit 15 controls processing so as to store a composite image created by the image compositing unit 13 into the image memory 14, and to display the composite image onto the monitor 3.

A process procedure of processing performed by the ultrasound diagnosis apparatus according to the second embodiment is similar to the first embodiment, except that processing corresponding to the processing of creating a second image at Step S504 in the process procedure of the processing performed by the ultrasound diagnosis apparatus according to the first embodiment explained with reference to FIG. 5 is the volume rendering processing to be performed after changing the color tone of a plane opposite to the projective plane in the three-dimensional ROI for valve observation, therefore explanations of the process procedure are omitted.

As described above, according to the second embodiment, when executing the volume rendering processing on a three-dimensional ultrasound image in an ROI for valve observation, a color tone of rendering a plane opposite to a projective plane of the ROI for valve observation is differentiated from the color of the projective plane; consequently, a part that the heart valve is not closed is clearly rendered as a background color on a second image, accordingly, visibility of an open-close state of the heart valve on an ultrasound image can be improved. Moreover, according to the second embodiment, because the ray tracing processing is not performed, a composite image for diagnostic imaging can be more speedily created and displayed by avoiding decrease in the realtime response, compared with the first embodiment.

Figure 9:
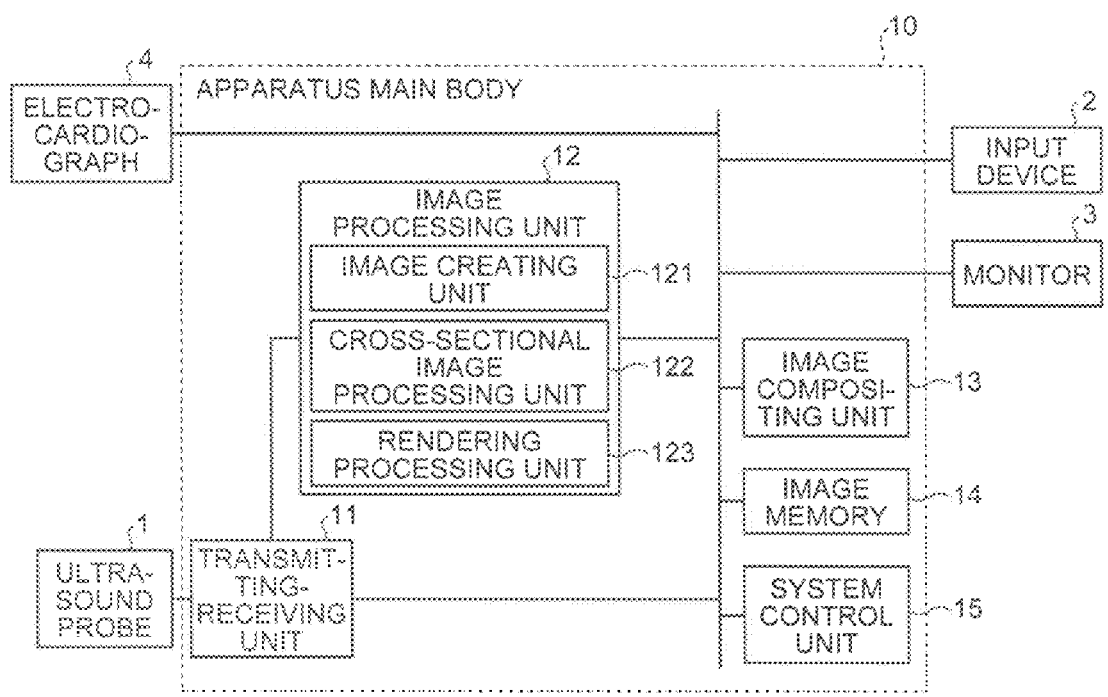
FIG. 9 is a schematic diagram for explaining a configuration of an ultrasound diagnosis apparatus according to a third embodiment of the present invention.

A third embodiment of the present invention is explained below in a case where a second image is created only in a specific phase, with reference to FIGS. 9 and 10. FIG. 9 is a schematic diagram for explaining a configuration of an ultrasound diagnosis apparatus according to the third embodiment; and FIG. 10 is a schematic diagram for explaining a phase in which a second image is created according to the third embodiment.

As shown in FIG. 9, although the ultrasound diagnosis apparatus according to the third embodiment has a configuration similar to that of the first embodiment, it is different from the first embodiment in point that the ultrasound diagnosis apparatus includes an electrocardiograph 4 that is attached to a subject, and measures an electrocardiogram waveform of the subject. The following description mainly explains this point.

A phase in which a mitral valve is closed is equivalent to a systole of a heart. For this reason, when diagnosing mitral regurgitation, observation of only a state in a systole is meaningful for a doctor as well as observing all phases of the heart along a time sequence.

Figure 10:
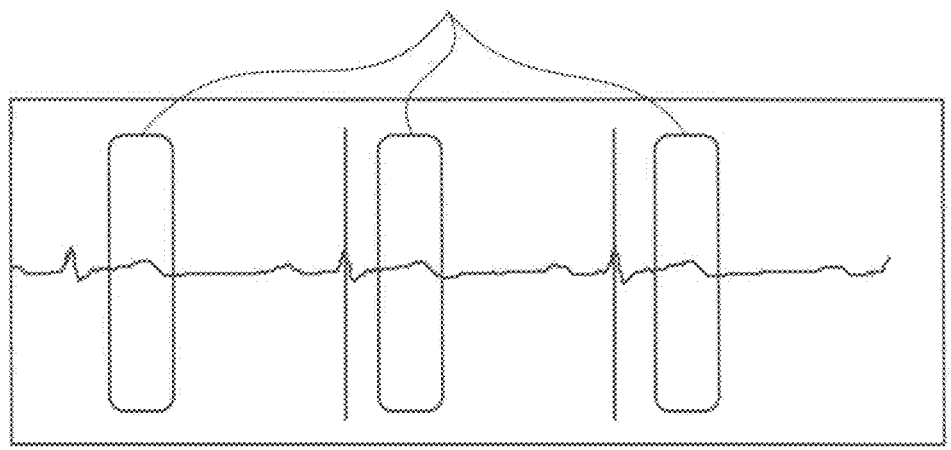
FIG. 10 is a schematic diagram for explaining a phase in which a second image is created according to the third embodiment.

Therefore, the system control unit 15 according to the third embodiment analyzes an electrocardiogram waveform measured by the electrocardiograph 4, and controls the ray-tracing processing unit 123b so as to create a second image through the ray tracing processing from a three-dimensional ultrasound image in an ROI for valve observation only in a period equivalent to a systole, as shown in FIG. 10.

Processing performed by the ultrasound diagnosis apparatus according to the third embodiment is explained below with reference to FIG. 11. FIG. 11 is a flowchart for explaining processing performed by the ultrasound diagnosis apparatus according to the third embodiment.

As shown in FIG. 11, according to the ultrasound diagnosis apparatus according to the third embodiment, when a scan is started, and then an ROI for display and an ROI for valve observation as well as a projecting direction are set on an MPR image of a three-dimensional ultrasound image by an operator via the input device 2 (Yes at Step S1101), the system control unit 15 converts "a two-dimensional ROI for display and a two-dimensional ROI for valve observation" into "a three-dimensional ROI for display and a three-dimensional ROI for valve observation", and then determines whether new volume data is created (Step S1102).

If new volume data is not created (No at Step S1102), the system control unit 15 waits until new volume data is created. By contrast, if new volume data is created (Yes at Step S1102), the system control unit 15 causes the rendering processing unit 123 and the image compositing unit 13 to start processing.

Precisely, under the control of the system control unit 15, the volume-rendering processing unit 123a creates a first image in the (three-dimensional) ROI for display through the volume rendering processing (Step S1103).

The system control unit 15 determines whether an electrocardiogram waveform at the present moment measured by the electrocardiograph 4 is the phase of a systole (Step S1104).

If the electrocardiogram waveform at the present moment is not the phase of a systole (No at Step S1105), the system control unit 15 controls processing so as to display only the first image (Step S1108).

By contrast, if the electrocardiogram waveform at the present moment is the phase of a systole (Yes at Step S1105), the ray-tracing processing unit 123b then creates a second image in the (three-dimensional) ROI for valve observation through the ray tracing processing, under the control of the system control unit 15 (Step S1105).

After that, the image compositing unit 13 creates a composite image by compositing the first image and the second image (Step S1106), and then the system control unit 15 controls processing so as to display the composite image created by the image compositing unit 13 on the monitor 3 (Step S1107).

After the processing at Step S1107 or the processing at Step S1108 is executed, the system control unit 15 then determines whether a scan termination request is received from the operator via the input device 2 (Step S1109); if scan termination request is not received (No at Step S1109), the system control unit 15 goes back to Step S1102, and waits until new volume data is created.

By contrast, if the scan termination request is received (Yes at Step S1109), the system control unit 15 terminates the processing.

Although the third embodiment is explained in a case where a case of displaying only a first image and a case of displaying a composite image are mixed, the present invention is not limited to this, and can be in a case of displaying only a composite image. In other words, it can be in a case where when the determination at Step S1102 is positive, determination processing of a phase is immediately performed; and then only if the phase is a systole, a first image, a second image, and a composite image are created, and only the composite image is displayed.

Moreover, although the third embodiment is explained in a case of creating a second image by the ray tracing processing, the present invention is not limited to this, and can be in a case of creating a second image by the volume rendering processing after changing the color tone of a background color as explained in the second embodiment.

Furthermore, although the third embodiment is explained in a case of creating a second image only in a specific phase and displaying a composite image, it can be in a case of creating a second image regardless of whether it is in the specific phase, and displaying a composite image only in the specific phase.

Moreover, although the third embodiment is explained in a case of diagnosing an open-close state of a mitral valve, the present invention is not limited to this, and can be in a case of diagnosing an open-close state of an aortic valve. In such case, a second image is created in a diastole of the heart.

As described above, according to the third embodiment, only a usual volume rendering image (first image) is displayed in a phase in which the heart valve opens, while a composite image is displayed in a phase in which the heart valve closes; as a result, only when the heart valve is not closed due to regurgitation, a leak of light is rendered on a ray tracing image (second image); accordingly, visibility of an open-close state of the heart valve on an ultrasound image can be further improved. Moreover, because the ray tracing processing is limited to a specific phase, compared with the first embodiment, decrease in the realtime response is further suppressed, and a composite image for diagnostic imaging can be more speedily created and displayed.

Furthermore, also when creating a second image of the specific phase by the method explained in the second embodiment, only a usual volume rendering image (first image) is displayed in a phase that the heart valve opens, so that the background color does not change if the heart valve is normally open, while a composite image is displayed in a phase that the heart valve closes; as a result, only when the heart valve is not closed due to regurgitation, a different background color is seen on the second image; accordingly, visibility of an open-close state of the heart valve on an ultrasound image can be further improved.

The first to third embodiments described above are explained in a case where an ultrasound diagnosis apparatus creates a first image, a second image, and a composite image, and then displays the created composite image. However, the present invention is not limited to this, and can be applied in a case where an image processing apparatus creates a first image, a second image, and a composite image by using a three-dimensional ultrasound image created by an ultrasound diagnosis apparatus, and then displays the composite image.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound diagnosis apparatus, comprising:
an ultrasound probe;
processing circuitry configured to
create a 3D ultrasound image from reflected wave data of an ultrasound wave transmitted to a subject from the ultrasound probe,
when a first region of interest that is a region of interest for displaying on a display the 3D ultrasound image and a second region of interest that is a region of interest included in the first region of interest and for observing a heart valve included in the 3D ultrasound image, and a projecting direction, are received from a computer interface,
create a first 2D image by performing volume rendering processing on the 3D ultrasound image in the first region of interest onto a projective plane along the projecting direction, and
create a second 2D image, on which motion of the heart valve can be identified, by performing ray tracing processing on the 3D ultrasound image in the second region of interest onto the projective plane along the projecting direction with a virtual light source positioned opposite to the projecting direction, and
cause the created first 2D image and the created second 2D image to be displayed in a superimposed manner on the display.

2. The ultrasound diagnosis apparatus according to claim 1, wherein the processing circuitry is further configured to create the second 2D image from a specific 3D ultrasound image in a specific phase from among a plurality of 3D ultrasound images created along a time sequence.

3. An ultrasound diagnosis apparatus, comprising:
an ultrasound probe;
processing circuitry configured to
create a 3D ultrasound image from reflected wave data of an ultrasound wave transmitted to a subject from the ultrasound probe,
when a first region of interest that is a region of interest for displaying on a display the 3D ultrasound image, and a second region of interest that is a region of interest included in the first region of interest and for observing a heart valve included in the 3D ultrasound image, and a projecting direction, are received from a computer interface,
create a first 2D image by performing volume rendering processing on the 3D ultrasound image in the first region of interest onto a projective plane along the projecting direction, and
create a second 2D image on which motion of the heart valve can be identified, by differentiating a color tone for rendering a plane opposite to the projective plane in the second region of interest from a color used for rendering the first 2D image, when performing volume rendering processing on the 3D ultrasound image in the second region of interest onto the projective plane along the projecting direction, and cause the created first 2D image and the created second 2D image to be displayed in a superimposed manner on the display.

4. The ultrasound diagnosis apparatus according to claim 3, wherein the processing circuitry is further configured to create the second 2D image from a specific 3D ultrasound image in a specific phase from among a plurality of 3D ultrasound images created along a time sequence.

5. An ultrasound image processing apparatus, comprising: processing circuitry configured to
   create a 3D ultrasound image from reflected wave data of an ultrasound wave transmitted to a subject from an ultra sound probe,
   when a first region of interest that is a region of interest for displaying on a display the 3D ultrasound image, and a second region of interest that is a region of interest included in the first region of interest and for observing a heart valve included in the 3D ultrasound image, and a projecting direction, are received from a computer interface,
       create a first 2D image by performing volume rendering processing on the 3D ultrasound image in the first region of interest onto a projective plane along the projecting direction, and
       create a second 2D image on which motion of the heart valve can be identified by performing ray tracing processing on the 3D ultrasound image in the second region of interest onto the projective plane along the projecting direction with a virtual light source positioned opposite to the projecting direction, and
   cause the created first 2D image and the created second 2D image to be displayed in a superimposed manner onto the display.

6. The ultrasound image processing apparatus according to claim 5, wherein the processing circuitry is further configured to create the second 2D image from a specific 3D ultrasound image in a specific phase from among a plurality of 3D ultrasound images created along a time sequence.

7. An ultrasound image processing apparatus, comprising: processing circuitry configured to
   create a 3D ultrasound image from reflected wave data of an ultrasound wave transmitted to a subject from an ultrasound probe, and
   when a first region of interest that is a region of interest for displaying on a display the 3D ultrasound image, and a second region of interest that is a region of interest included in the first region of interest and for observing a heart valve included in the 3D ultrasound image, and a projecting direction, are received from a computer interface,
       create a first 2D image by performing volume rendering processing on the 3D ultrasound image in the first region of interest onto a projective plane along the projecting direction, and
       create a second 2D image, on which motion of the heart valve can be identified, by differentiating a color tone for rendering a plane opposite to the projective plane in the second region of interest from a color used for rendering the first 2D image, when performing volume rendering processing on the 3D ultrasound image in the second region of interest onto the projective plane along the projecting direction, and cause the created first 2D image and the created second 2D image to be displayed in a superimposed manner on the display.

8. The ultrasound image processing apparatus according to claim 7, wherein the processing circuitry is further configured to create the second 2D image from a specific 3D ultrasound image in a specific phase from among a plurality of 3D ultrasound images created along a time sequence.

9. An image processing method, comprising:
   creating a 3D ultrasound image from reflected wave data of an ultrasound wave transmitted to a subject from an ultrasound probe;
   creating a first 2D image by performing volume rendering processing onto a projective plane along a projecting direction on the 3D ultrasound image in a first region of interest that is a region of interest for displaying on a display the 3D ultrasound image;
   creating a second 2D image, on which motion of a heart valve included in the 3D ultrasound image can be identified, by performing ray tracing processing on the 3D ultrasound image in a second region of interest that is a region of interest included in the first region of interest and for observing the heart valve onto the projective plane along the projecting direction with a virtual light source positioned opposite to the projecting direction, when receiving the first region of interest and the second region of interest as well as the projecting direction from a computer interface; and
   displaying the created first 2D image and the created second 2D image in a superimposed manner on the display.

10. The image processing method according to claim 9, wherein the second 2D image is created from a specific 3D ultrasound image in a specific phase from among a plurality of 3D ultrasound images created along a time sequence.

11. An image processing method, comprising:
   creating a 3D ultrasound image from reflected wave data of an ultrasound wave transmitted to a subject from an ultrasound probe;
   creating a first 2D image by performing volume rendering processing onto a projective plane along a projecting direction on the 3D ultrasound image in a first region of interest that is a region of interest for displaying on a display the 3D ultrasound image;
   creating a second 2D image, on which motion of a heart valve included in the 3D ultrasound image can be identified, by differentiating a color tone for rendering a plane opposite to the projective plane in a second region of interest, that is a region of interest included in the first region of interest and for observing the heart valve, from a color used for rendering the first 2D image, when performing volume rendering processing on the 3D ultrasound image in the second region of interest onto the projective plane along the projecting direction, when receiving the first region of interest and the second region of interest as well as the projecting direction from a computer interface; and
   displaying the created first 2D image and the created second 2D image in a superimposed manner onto the display.

12. The image processing method according to claim 11, wherein the second 2D image is created from a specific 3D ultrasound image in a specific phase from among a plurality of 3D ultrasound images created along a time sequence.

* * * * *